United States Patent
Lakin et al.

(10) Patent No.: US 8,934,961 B2
(45) Date of Patent: Jan. 13, 2015

(54) TRACKABLE DIAGNOSTIC SCOPE APPARATUS AND METHODS OF USE

(75) Inventors: Ryan Cameron Lakin, Newton, NJ (US); Kevin Stone, Winona Lake, IN (US); Christina Lakin, Newton, NJ (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1413 days.

(21) Appl. No.: 12/123,094

(22) Filed: May 19, 2008

(65) Prior Publication Data

US 2008/0306490 A1    Dec. 11, 2008

Related U.S. Application Data

(60) Provisional application No. 60/938,771, filed on May 18, 2007.

(51) Int. Cl.
```
A61B 5/05      (2006.01)
G06K 9/00      (2006.01)
A61B 17/56     (2006.01)
A61B 19/00     (2006.01)
```
(Continued)

(52) U.S. Cl.
CPC ............. *A61B 19/5244* (2013.01); *A61B 5/064* (2013.01); *A61B 19/52* (2013.01); *A61B 1/04* (2013.01); *A61B 1/317* (2013.01); *A61B 19/56* (2013.01); *A61B 2019/505* (2013.01); *A61B 2019/508* (2013.01); *A61B 2019/5231* (2013.01); *A61B 2019/5238* (2013.01); *A61B 2019/5255* (2013.01); *A61B 2019/5268* (2013.01); *A61B 2019/5483* (2013.01)

USPC .......... 600/426; 600/407; 600/424; 382/128; 606/53

(58) Field of Classification Search
USPC .......... 600/407, 424, 414, 426; 623/901, 911, 623/914, 16.11; 382/128; 606/53, 86
See application file for complete search history.

(56) References Cited

U.S. PATENT DOCUMENTS 3,541,541 A    11/1970   Engelbart
4,341,220 A    7/1982    Perry
(Continued)

FOREIGN PATENT DOCUMENTS

EP    0 427 358    5/1991
EP    0 649 117    4/1995
(Continued)

OTHER PUBLICATIONS

Muller PE, Pellengahr C, Witt M, Kircher J, Refior HJ, Jansson V. Influence of minimally invasive surgery on implant positioning and the functional outcome for medial unicompartmental knee arthroplasty. J Arthroplasty 2004; 19(3): 296-301.

(Continued)

*Primary Examiner* — Katherine Fernandez
(74) *Attorney, Agent, or Firm* — Taft Stettinius and Hollister LLP; Ryan O. White

(57) ABSTRACT

A surgical procedure is provided. The procedure acquires a plurality of points on or near a bone abnormality and registers them with a surgical navigation system. The navigation system uses the acquired points to make an implant having a surface adapted to contact the bone, and particularly an implant having a portion whose shape substantially matches that of the bone abnormality.

11 Claims, 9 Drawing Sheets

(51) Int. Cl.
*A61B 5/06* (2006.01)
*A61B 1/04* (2006.01)
*A61B 1/317* (2006.01)

(56) References Cited

U.S. PATENT DOCUMENTS

| | | | |
|---|---|---|---|
| 4,360,028 A | 11/1982 | Barbier et al. | |
| 4,583,538 A | 4/1986 | Onik et al. | |
| 4,791,934 A | 12/1988 | Brunnett | |
| 4,945,914 A | 8/1990 | Allen | |
| 4,991,579 A | 2/1991 | Allen | |
| 5,016,639 A | 5/1991 | Allen | |
| 5,094,241 A | 3/1992 | Allen | |
| 5,097,839 A | 3/1992 | Allen | |
| 5,119,817 A | 6/1992 | Allen | |
| 5,142,930 A | 9/1992 | Allen et al. | |
| 5,178,164 A | 1/1993 | Allen | |
| 5,182,641 A | 1/1993 | Diner et al. | |
| 5,211,164 A | 5/1993 | Allen | |
| 5,222,499 A | 6/1993 | Allen et al. | |
| 5,230,338 A | 7/1993 | Allen et al. | |
| 5,230,623 A | 7/1993 | Guthrie et al. | |
| 5,261,404 A | 11/1993 | Mick et al. | |
| 5,309,913 A | 5/1994 | Kormos et al. | |
| 5,383,454 A | 1/1995 | Bucholz | |
| 5,389,101 A | 2/1995 | Heilbrun et al. | |
| 5,397,329 A | 3/1995 | Allen | |
| 5,517,990 A | 5/1996 | Kalfas et al. | |
| 5,603,318 A | 2/1997 | Heilbrun et al. | |
| 5,628,315 A | 5/1997 | Vilsmeier et al. | |
| 5,631,973 A | 5/1997 | Green | |
| 5,638,819 A | 6/1997 | Manwaring et al. | |
| 5,682,886 A | 11/1997 | Delp et al. | |
| 5,682,890 A | 11/1997 | Kormos et al. | |
| 5,704,897 A | 1/1998 | Truppe | |
| 5,724,985 A | 3/1998 | Snell et al. | |
| 5,732,703 A | 3/1998 | Kalfas et al. | |
| 5,740,802 A | 4/1998 | Nafis et al. | |
| 5,769,861 A | 6/1998 | Vilsmeier | |
| 5,772,594 A | 6/1998 | Barrick | |
| 5,776,064 A | 7/1998 | Kalfas et al. | |
| 5,799,055 A | 8/1998 | Peshkin et al. | |
| 5,835,791 A | 11/1998 | Goff et al. | |
| 5,836,954 A | 11/1998 | Heilbrun et al. | |
| 5,851,183 A | 12/1998 | Bucholz | |
| 5,871,018 A | 2/1999 | Delp et al. | |
| 5,902,239 A | 5/1999 | Buurman | |
| 5,967,982 A | 10/1999 | Barnett | |
| 5,980,535 A | 11/1999 | Barnett et al. | |
| 5,987,960 A | 11/1999 | Messner et al. | |
| 5,999,837 A | 12/1999 | Messner et al. | |
| 6,021,343 A | 2/2000 | Foley et al. | |
| 6,069,932 A | 5/2000 | Peshkin et al. | |
| 6,122,541 A | 9/2000 | Cosman et al. | |
| 6,135,946 A | 10/2000 | Konen et al. | |
| 6,162,227 A | 12/2000 | Eckhardt et al. | |
| 6,167,145 A | 12/2000 | Foley et al. | |
| 6,178,345 B1 | 1/2001 | Vilsmeier et al. | |
| 6,190,395 B1 | 2/2001 | Williams | |
| 6,198,794 B1 | 3/2001 | Peshkin et al. | |
| 6,205,411 B1 | 3/2001 | DiGioia, III et al. | |
| 6,226,548 B1 | 5/2001 | Foley et al. | |
| 6,235,038 B1 | 5/2001 | Hunter et al. | |
| 6,236,875 B1 | 5/2001 | Bucholz et al. | |
| 6,285,902 B1 | 9/2001 | Kienzle, III et al. | |
| 6,306,126 B1 | 10/2001 | Moctezuma | |
| 6,333,971 B2 * | 12/2001 | McCrory et al. | 378/162 |
| 6,340,979 B1 | 1/2002 | Beaton et al. | |
| 6,358,253 B1 | 3/2002 | Torrie et al. | |
| 6,368,279 B1 | 4/2002 | Liu | |
| 6,377,839 B1 | 4/2002 | Kalfas et al. | |
| 6,379,302 B1 | 4/2002 | Kessman et al. | |
| 6,381,485 B1 | 4/2002 | Hunter et al. | |
| 6,390,982 B1 | 5/2002 | Bova et al. | |
| 6,402,762 B2 | 6/2002 | Hunter et al. | |
| 6,424,856 B1 | 7/2002 | Vilsmeier et al. | |
| 6,428,547 B1 | 8/2002 | Vilsmeier et al. | |
| 6,434,415 B1 | 8/2002 | Foley et al. | |
| 6,434,507 B1 | 8/2002 | Clayton et al. | |
| 6,440,141 B1 | 8/2002 | Philippon | |
| 6,470,207 B1 | 10/2002 | Simon et al. | |
| 6,490,467 B1 | 12/2002 | Bucholz et al. | |
| 6,491,699 B1 | 12/2002 | Henderson et al. | |
| 6,520,964 B2 | 2/2003 | Tallarida et al. | |
| 6,527,443 B1 | 3/2003 | Vilsmeier et al. | |
| 6,535,756 B1 | 3/2003 | Simon et al. | |
| 6,553,152 B1 | 4/2003 | Miller et al. | |
| 6,584,174 B2 | 6/2003 | Schubert et al. | |
| 6,591,130 B2 | 7/2003 | Shahidi | |
| 6,591,581 B2 | 7/2003 | Schmieding | |
| 6,607,487 B2 | 8/2003 | Chang et al. | |
| 6,609,022 B2 | 8/2003 | Vilsmeier et al. | |
| 6,612,980 B2 | 9/2003 | Chen et al. | |
| 6,636,763 B1 | 10/2003 | Junker et al. | |
| 6,674,916 B1 | 1/2004 | Deman et al. | |
| 6,695,772 B1 | 2/2004 | Bon et al. | |
| 6,697,664 B2 | 2/2004 | Kienzle, III et al. | |
| 6,712,856 B1 | 3/2004 | Carignan et al. | |
| 6,714,629 B2 | 3/2004 | Vilsmeier | |
| 6,724,922 B1 | 4/2004 | Vilsmeier | |
| 6,725,080 B2 | 4/2004 | Melkent et al. | |
| 6,725,082 B2 | 4/2004 | Sati et al. | |
| 6,754,374 B1 | 6/2004 | Miller et al. | |
| 6,772,002 B2 | 8/2004 | Schmidt et al. | |
| 6,776,526 B2 | 8/2004 | Zeiss | |
| 6,782,287 B2 | 8/2004 | Grzeszczuk et al. | |
| 6,783,549 B1 | 8/2004 | Stone et al. | |
| 6,811,313 B2 | 11/2004 | Graumann et al. | |
| 6,852,114 B2 | 2/2005 | Cerundolo | |
| 6,856,826 B2 | 2/2005 | Seeley et al. | |
| 6,856,827 B2 | 2/2005 | Seeley et al. | |
| 6,856,828 B2 | 2/2005 | Cossette et al. | |
| 6,887,245 B2 | 5/2005 | Kienzle, III et al. | |
| 6,887,247 B1 | 5/2005 | Couture et al. | |
| 6,892,088 B2 | 5/2005 | Faulkner et al. | |
| 6,895,268 B1 | 5/2005 | Rahn et al. | |
| 6,896,657 B2 | 5/2005 | Willis | |
| 6,917,827 B2 | 7/2005 | Kienzle, III | |
| 6,920,347 B2 | 7/2005 | Simon et al. | |
| 6,925,339 B2 | 8/2005 | Grimm et al. | |
| 6,926,673 B2 | 8/2005 | Roberts et al. | |
| 6,932,823 B2 | 8/2005 | Grimm et al. | |
| 6,947,582 B1 | 9/2005 | Vilsmeier et al. | |
| 6,947,783 B2 | 9/2005 | Immerz | |
| 6,950,689 B1 | 9/2005 | Willis et al. | |
| 6,978,166 B2 | 12/2005 | Foley et al. | |
| 6,988,009 B2 | 1/2006 | Grimm et al. | |
| 6,990,220 B2 | 1/2006 | Ellis et al. | |
| 7,008,430 B2 | 3/2006 | Dong et al. | |
| 7,010,095 B2 | 3/2006 | Mitschke et al. | |
| 7,097,357 B2 * | 8/2006 | Johnson et al. | 378/205 |
| 7,949,386 B2 * | 5/2011 | Buly et al. | 600/427 |
| 2001/0007918 A1 | 7/2001 | Vilsmeier et al. | |
| 2001/0011175 A1 | 8/2001 | Hunter et al. | |
| 2001/0036245 A1 | 11/2001 | Kienzle, III et al. | |
| 2001/0051881 A1 | 12/2001 | Filler | |
| 2002/0077540 A1 | 6/2002 | Kienzle, III | |
| 2002/0095081 A1 | 7/2002 | Vilsmeier | |
| 2002/0095083 A1 | 7/2002 | Cinquin et al. | |
| 2002/0099288 A1 | 7/2002 | Chang et al. | |
| 2002/0183610 A1 | 12/2002 | Foley et al. | |
| 2003/0055502 A1 | 3/2003 | Lang et al. | |
| 2003/0059097 A1 | 3/2003 | Abovitz et al. | |
| 2003/0071893 A1 | 4/2003 | Miller et al. | |
| 2003/0181806 A1 | 9/2003 | Medan et al. | |
| 2003/0209096 A1 | 11/2003 | Pandey et al. | |
| 2003/0216669 A1 | 11/2003 | Lang et al. | |
| 2004/0015077 A1 | 1/2004 | Sati et al. | |
| 2004/0030245 A1 | 2/2004 | Noble et al. | |
| 2004/0087852 A1 | 5/2004 | Chen et al. | |
| 2004/0097952 A1 | 5/2004 | Sarin et al. | |
| 2004/0127788 A1 | 7/2004 | Arata | |
| 2004/0133276 A1 | 7/2004 | Lang et al. | |
| 2004/0138754 A1 * | 7/2004 | Lang et al. | 623/20.14 |

(56) References Cited

U.S. PATENT DOCUMENTS

| | | |
|---|---|---|
| 2004/0141015 A1 | 7/2004 | Fitzmaurice et al. |
| 2004/0151354 A1 | 8/2004 | Leitner et al. |
| 2004/0167390 A1 | 8/2004 | Alexander et al. |
| 2004/0169673 A1 | 9/2004 | Crampe et al. |
| 2004/0254454 A1 | 12/2004 | Kockro |
| 2004/0267242 A1 | 12/2004 | Grimm et al. |
| 2005/0015003 A1 | 1/2005 | Lachner et al. |
| 2005/0015005 A1 | 1/2005 | Kockro |
| 2005/0015022 A1 | 1/2005 | Richard et al. |
| 2005/0015099 A1 | 1/2005 | Momoi et al. |
| 2005/0020909 A1 | 1/2005 | Moctezuma de la Barrera et al. |
| 2005/0020911 A1 | 1/2005 | Viswanathan et al. |
| 2005/0021037 A1 | 1/2005 | McCombs et al. |
| 2005/0021039 A1 | 1/2005 | Cusick et al. |
| 2005/0021043 A1 | 1/2005 | Jansen et al. |
| 2005/0021044 A1 | 1/2005 | Stone et al. |
| 2005/0024323 A1 | 2/2005 | Salazar-Ferrer et al. |
| 2005/0033117 A1 | 2/2005 | Ozaki et al. |
| 2005/0033149 A1 | 2/2005 | Strommer et al. |
| 2005/0038337 A1 | 2/2005 | Edwards |
| 2005/0049477 A1 | 3/2005 | Fu et al. |
| 2005/0049478 A1 | 3/2005 | Kuduvalli et al. |
| 2005/0049485 A1 | 3/2005 | Harmon et al. |
| 2005/0049486 A1 | 3/2005 | Urquhart et al. |
| 2005/0054915 A1 | 3/2005 | Sukovic et al. |
| 2005/0054916 A1 | 3/2005 | Mostafavi |
| 2005/0059873 A1 | 3/2005 | Glozman et al. |
| 2005/0075632 A1 | 4/2005 | Russell et al. |
| 2005/0080334 A1 | 4/2005 | Willis |
| 2005/0085714 A1 | 4/2005 | Foley et al. |
| 2005/0085715 A1 | 4/2005 | Dukesherer et al. |
| 2005/0085717 A1 | 4/2005 | Shahidi |
| 2005/0085718 A1 | 4/2005 | Shahidi |
| 2005/0085720 A1 | 4/2005 | Jascob et al. |
| 2005/0090730 A1 | 4/2005 | Cortinovis et al. |
| 2005/0090733 A1 | 4/2005 | Van Der Lugt et al. |
| 2005/0096515 A1 | 5/2005 | Geng |
| 2005/0096535 A1 | 5/2005 | de la Barrera |
| 2005/0101970 A1 | 5/2005 | Rosenberg |
| 2005/0113659 A1 | 5/2005 | Pothier et al. |
| 2005/0113960 A1 | 5/2005 | Karau et al. |
| 2005/0119561 A1 | 6/2005 | Kienzle, III |
| 2005/0119565 A1 | 6/2005 | Pescatore |
| 2005/0119639 A1 | 6/2005 | McCombs et al. |
| 2005/0119783 A1 | 6/2005 | Brisson et al. |
| 2005/0124988 A1 | 6/2005 | Terrill-Grisoni et al. |
| 2005/0137599 A1 | 6/2005 | Masini |
| 2005/0137600 A1 | 6/2005 | Jacobs et al. |
| 2005/0148850 A1 | 7/2005 | Lahm et al. |
| 2005/0148855 A1 | 7/2005 | Kienzle, III |
| 2005/0197568 A1 | 9/2005 | Vass et al. |
| 2005/0197569 A1 | 9/2005 | McCombs |
| 2005/0203373 A1 | 9/2005 | Boese et al. |
| 2005/0203374 A1 | 9/2005 | Vilsmeier |
| 2005/0203375 A1 | 9/2005 | Willis et al. |
| 2005/0203383 A1 | 9/2005 | Moctezuma de la Barrera et al. |
| 2005/0203384 A1 | 9/2005 | Sati et al. |
| 2005/0215879 A1 | 9/2005 | Chuanggui |
| 2005/0215888 A1 | 9/2005 | Grimm et al. |
| 2005/0216032 A1 | 9/2005 | Hayden |
| 2005/0228250 A1 | 10/2005 | Bitter et al. |
| 2005/0228266 A1 | 10/2005 | McCombs |
| 2005/0228270 A1 | 10/2005 | Lloyd et al. |
| 2005/0228404 A1 | 10/2005 | Vandevelde |
| 2005/0234335 A1 | 10/2005 | Simon et al. |
| 2005/0234465 A1 | 10/2005 | McCombs et al. |
| 2005/0251026 A1 | 11/2005 | Stone |
| 2005/0251030 A1 | 11/2005 | Azar et al. |
| 2005/0267353 A1 | 12/2005 | Marquart et al. |
| 2005/0267354 A1 | 12/2005 | Marquart et al. |
| 2005/0267358 A1 | 12/2005 | Tuma et al. |
| 2005/0267360 A1 | 12/2005 | Birkenbach et al. |
| 2005/0267365 A1 | 12/2005 | Sokulin et al. |
| 2005/0267722 A1 | 12/2005 | Marquart et al. |
| 2005/0277832 A1 | 12/2005 | Foley et al. |
| 2005/0279368 A1 | 12/2005 | McCombs |
| 2005/0281465 A1 | 12/2005 | Marquart et al. |
| 2005/0288575 A1 | 12/2005 | de la Barrera et al. |
| 2005/0288578 A1 | 12/2005 | Durlak |
| 2006/0004284 A1 | 1/2006 | Grunschlager et al. |
| 2006/0009780 A1 | 1/2006 | Foley et al. |
| 2006/0015018 A1 | 1/2006 | Jutras et al. |
| 2006/0015030 A1 | 1/2006 | Poulin et al. |
| 2006/0025677 A1 | 2/2006 | Verard et al. |
| 2006/0025679 A1 | 2/2006 | Viswanathan et al. |
| 2006/0025681 A1 | 2/2006 | Abovitz et al. |
| 2006/0036149 A1 | 2/2006 | Lavigna et al. |
| 2006/0036151 A1 | 2/2006 | Ferre et al. |
| 2006/0036162 A1 | 2/2006 | Shahidi et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0052691 A1 | 3/2006 | Hall et al. |
| 2006/0058604 A1 | 3/2006 | Avinash et al. |
| 2006/0058615 A1 | 3/2006 | Mahajan et al. |
| 2006/0058616 A1 | 3/2006 | Marquart et al. |
| 2006/0058644 A1 | 3/2006 | Hoppe et al. |
| 2006/0058646 A1 | 3/2006 | Viswanathan |
| 2006/0058663 A1 | 3/2006 | Willis et al. |
| 2007/0016008 A1* | 1/2007 | Schoenefeld ............... 600/424 |

FOREIGN PATENT DOCUMENTS

| | | |
|---|---|---|
| EP | 0 832 609 | 4/1998 |
| EP | 0 904 735 | 3/1999 |
| EP | 1 226 788 | 7/2002 |
| GB | 2 246 936 | 2/1992 |
| WO | WO 02/35454 | 5/2002 |
| WO | WO 02/062248 | 8/2002 |
| WO | WO 02/067783 | 9/2002 |
| WO | WO 04/001569 | 12/2003 |
| WO | WO 2004/006770 | 1/2004 |
| WO | WO 2004/069036 | 8/2004 |
| WO | WO 2004/069040 | 8/2004 |

OTHER PUBLICATIONS

"A Computer-Assisted Total Knee Replacement Surgical System Using a Calibrated Robot," Thomas C. Kienzle III, S. David Stulburg, Michael Peshkin, Arthur Quaid, Jon Lea, Ambarish Goswami, and Chi-Haur Wu, in "Computer-Integrated Surgery: Technology and Clinical Applications," ed. Russell H. Taylor, et. al., 1996 MIT Press. (28 pages).

"Real-Time Image Segmentation for Image-Guided Surgery" by Warfield, Simon; 14 pages; http://splweb.bwh.harvard.edu:8000/pages/papers/warfield/sc98/; accepted to appear at SC98.

"Acumen™ Surgical Navigation System, Surgical Navigation Applications" (2003) (2 pages).

Acumen™ Surgical Navigation System, Understanding Surgical Navigation (2003) (2 pages).

Bathis H, Perlick L, Tingart M, Luring C, Zurakowski D, Grifka J. Alignment in total knee arthroplasty. A comparison of computer-assisted surgery with the conventional technique. J Bone Joint Surg Br. 2004;86(5):682-687.

C. Graetzel, T.W. Fong, S. Grange, and C. Baur, "A non-contact mouse for surgeon-computer interaction," Technology and Health Care, vol. 12, No. 3, 2004, pp. 245-257.

Chauhan SK, Clark GW, Lloyd S, Scott RG, Breidhal W, Sikorski JM. Computer-assisted total knee replacement: a controlled cadaver study using a multi-parameter quantitative CT assessment of alignment (the Perth CT Protocol). J Bone Joint Surg [BR] 2004;86-B:818-23.

David Stulberg S. How accurate is current TKR instrumentation? Clin Orthop. Nov. 2003;(416):177-84.

DiFranco. D.E. et al., "Recovery of 3D Articulated Motion from 2D Correspondences," Cambridge Research Laboratory Technical Report CRL 99/7, Dec. 1999 (20 pages).

DiGioia AM, Jaramaz B; Colgan BD. Computer assisted orthopaedic surgery. Image guided and robotic assistive technologies. Clin Orthop Sep. 1998;(354):8-16.

(56) References Cited

OTHER PUBLICATIONS

Donald G. Eckhoff, Joel M. Bach, Victor M. Spitzer, Karl D. Reinig, Michelle M. Bagur, Todd H. Baldini, David Rubinstein, and Stephen Humphries, "Three-Dimensional Morphology and Kinematics of the Distal Part of the Femur Viewed in Virtual Reality. Part II," J Bone Joint Surg. Am 2003 85(Supp 4): 97-104.

Habets, R.J.E.: *Computer assistance in orthopaedic surgery.* Promoters: prof dr.ir. A. Hasman, prof.dr.ir. F.A. Gerritsen; copromoter: dr.ir. J.A. Blom. Technische Universiteit Eindhoven, ISBN 90-386-1940-5, Nov. 4, 2002. (4 pages).

James B. Stiehl et al., Navigation and Robotics in Total Joint and Spine Surgery, Chapter 1 Basics of Computer-Assisted Orthopedic Surgery (CAOS), Springer-Verlag (2004) (9 pages).

James B. Stiehl et al., Navigation and Robotics in Total Joint and Spine Surgery, Chapter 3 C-Arm-Based Navigation, Springer-Verlag (2004) (9 pages).

Langlotz, F., et al., Femoral Stem navigation with the Surgi-GATE System, Navigation and Robotics in Total Joint and Spine Surgery, 2004, Springer, Chapter 13, p. 102-109.

Luck, J.P., Debrunner, C., Hoff, W., He, Q., and Small, D. "Development and Analysis of a Real-Time Human Motion Tracking System," in *Proc. of Workshop on Applications of Computer Vision.* 2002. Orlando, FL, IEEE (7 pages).

Traxtal Technologies—Virtual Keypad, (printed May 23, 2005) pp. 1-2, http://www.traxtal.com/products/products_input_virtualkeypad.htm?print.

Visarius H, Gong J, Scheer C, Haralamb S, Nolte LP, Man-machine interfaces in computer assisted surgery. Comput Aid Surg 1997;2:102-107.

* cited by examiner

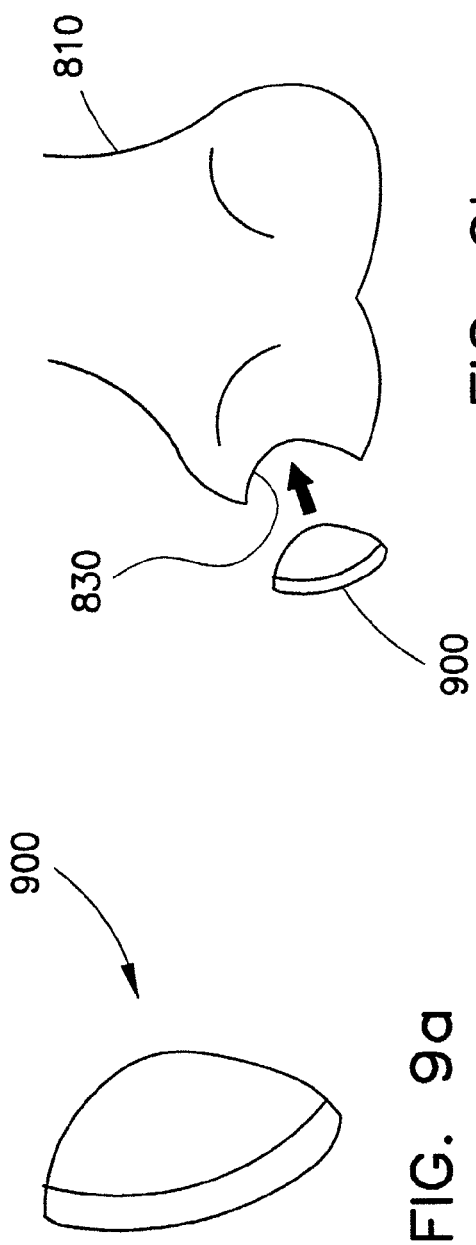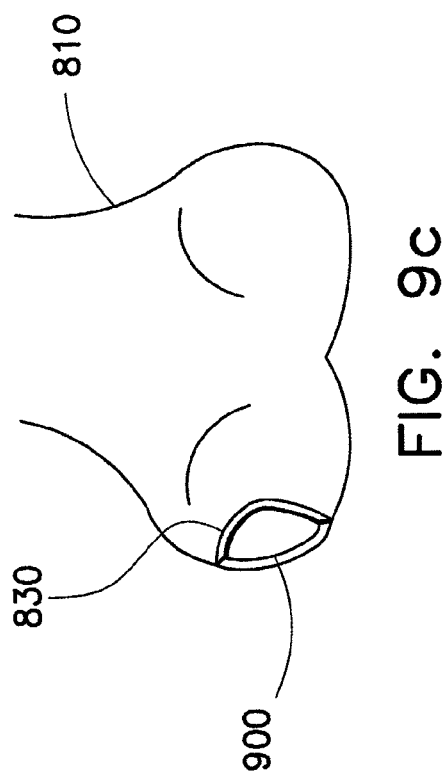

TRACKABLE DIAGNOSTIC SCOPE APPARATUS AND METHODS OF USE

RELATED APPLICATIONS

This application claims priority to U.S. Provisional Application Ser. No. 60/938,771 filed May 18, 2007, the entire contents of which are hereby incorporated by reference in their entirety.

BACKGROUND

The present teachings relate generally to surgical navigation, and more particularly to a method for surgically navigating a trackable diagnostic scope along the surface of a bone to identify defects or abnormalities.

Surgical navigation systems, also known as computer assisted surgery and image guided surgery, aid surgeons in locating patient anatomical structures, guiding surgical instruments, and implanting medical devices with a high degree of accuracy. Surgical navigation has been compared to a global positioning system that aids vehicle operators to navigate the earth. A surgical navigation system typically includes a computer, a tracking system, and patient anatomical information. The patient anatomical information can be obtained by using an imaging mode such as fluoroscopy, computer tomography (CT) or by simply defining the location of patient anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during a surgical procedure utilizing surgical navigation, surgeons often use "tracking arrays" that are coupled to the surgical components. These tracking arrays allow the surgeons to track the physical location of these surgical components, as well as the patient's bones during the surgery. By knowing the physical location of the tracking array, software associated with the tracking system can accurately calculate the position of the tracked component relative to a surgical plan image.

It is known to use surgical navigation instruments to measure the size and general contour of a bone for use in the selection or manufacture of a prosthetic implant. This selection process allows the surgeon to choose a prosthetic implant that comfortably fits the general shape and size of the patient's anatomy. It would be desirable to improve upon these methods to reduce surgery time and improve prosthetic fit and/or function.

SUMMARY OF THE INVENTION

The present teachings provide a trackable diagnostic scope apparatus that is capable of identifying defects or abnormalities on the surface of a bone. These defects or abnormalities are registered by the surgical navigation system and then analyzed so that a prosthetic device can be custom manufactured to fit the flawed surface of the bone in a precise manner.

In one exemplary embodiment, the present teachings provide a method of performing a surgical procedure. The method comprises providing a tracking system and a diagnostic scope trackable by the tracking system, identifying an abnormality on a bone with the diagnostic scope, and acquiring a plurality of points on or near the abnormality with the diagnostic scope. The acquired points are then used to make an implant having a portion whose shape substantially matches that of the bone abnormality.

According to another exemplary embodiment herein, an image guided surgery system is provided. The system comprises a computer having surgical navigation utilities software, a tracking system having a measurement field, and a diagnostic scope that is trackable by the tracking system when exposed to the measurement field. The software comprises a program that when executed causes the system to acquire a plurality of points on or near the abnormality to make an implant having a portion whose shape substantially matches that of the bone abnormality.

In yet another exemplary embodiment, a computer readable storage medium is provided. According to this embodiment, the storage medium stores instructions that, when executed by a computer, causes the computer to perform a surgical procedure. The surgical procedure comprises tracking a diagnostic scope with a tracking system when the diagnostic scope is exposed to a measurement field of the tracking system, and making an implant having a portion whose shape substantially matches that of the bone abnormality by acquiring a plurality of points on or near the abnormality with the diagnostic scope.

BRIEF DESCRIPTION OF THE DRAWINGS

The above-mentioned aspects of the present teachings and the manner of obtaining them will become more apparent and the invention itself will be better understood by reference to the following description of the embodiments of the invention taken in conjunction with the accompanying drawings, wherein:

FIG. 9a is a perspective view of a custom manufactured implant device in accordance with the present teachings;

FIG. 9b is a perspective view of the implant device of FIG. 9a aligned with a bone prior to being implanted thereon; and FIG. 9c is a perspective view of the implant device of FIG. 9a shown implanted onto the bone.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
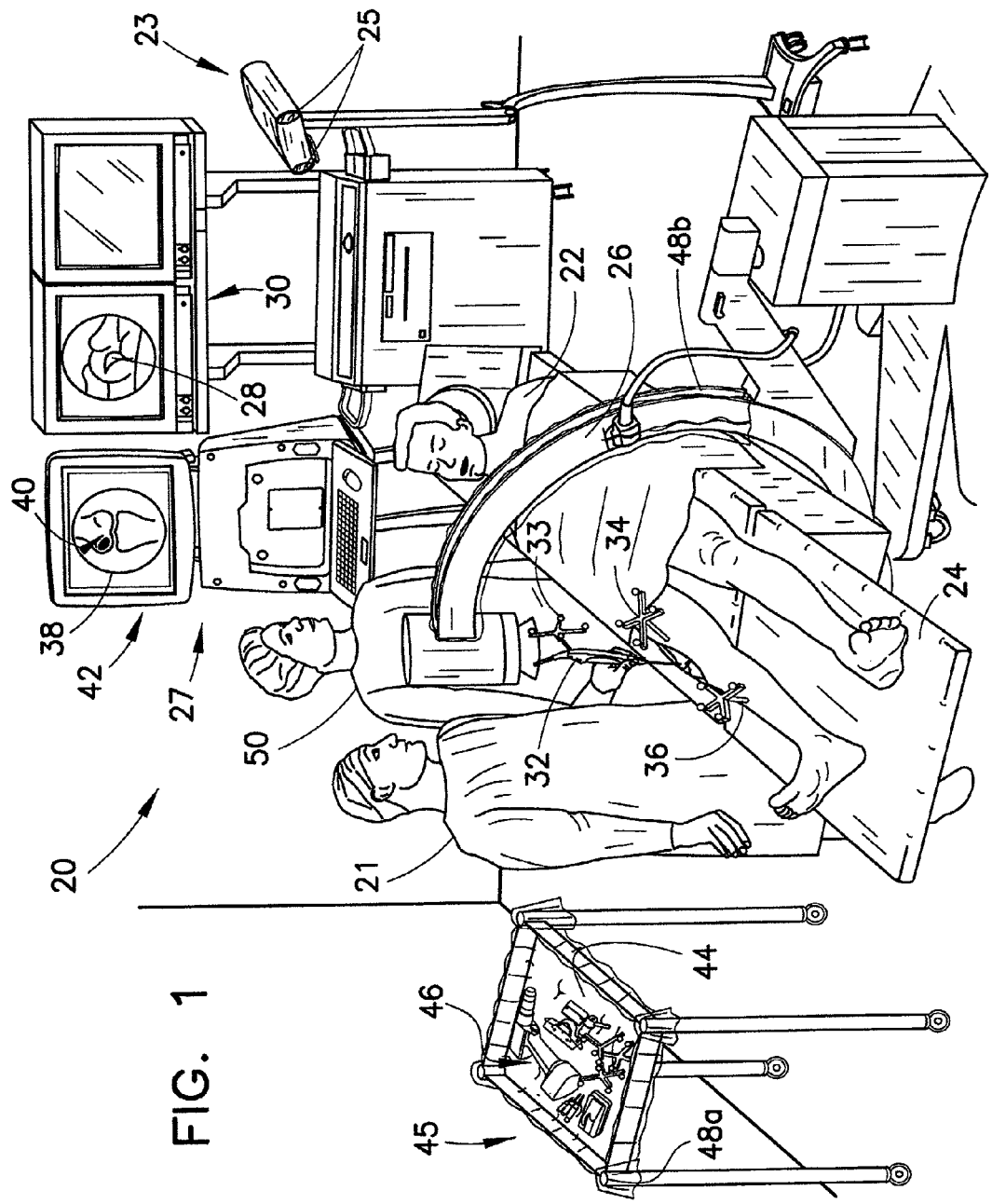
FIG. 1 is a perspective view of an exemplary operating room setup in a surgical navigation embodiment in accordance with the present teachings.

FIG. 1 shows a perspective view of an operating room with surgical navigation system 20. Surgeon 21 is aided by the surgical navigation system in performing knee arthroplasty, also known as knee replacement surgery, on patient 22 shown lying on operating table 24. Surgical navigation system 20 has a tracking system that locates arrays and tracks them in real-time. To accomplish this, the surgical navigation system includes optical locator 23, which has two CCD (charge couple device) cameras 25 that detect the positions of the arrays in space by using triangulation methods. The relative location of the tracked arrays, including the patient's anatomy, can then be shown on a computer display (such as computer display 27 for instance) to assist the surgeon during the surgical procedure. The arrays that are typically used include probe arrays, instrument arrays, reference arrays, and calibrator arrays. The operating room includes an imaging system such as C-arm fluoroscope 26 with fluoroscope display image 28 to show a real-time image of the patient's knee on monitor 30. The tracking system also detects the location of diagnostic scope 32 including its reference array 33, as well as reference arrays 34, 36, which are attached to the patient's femur and tibia, respectively. The relative location of diagnostic scope 32 to the patient's femur is shown as reference numeral 40 on computer display image 38 of computer monitor 42. The operating room also includes instrument cart 45 having tray 44 for holding a variety of surgical instruments and arrays 46. Instrument cart 45 and C-arm 26 are typically draped in sterile covers 48a, 48b to eliminate contamination risks within the sterile field.

The surgery is performed within a sterile field, adhering to the principles of asepsis by all scrubbed persons in the operating room. Patient 22, surgeon 21 and assisting clinician 50 are prepared for the sterile field through appropriate scrubbing and clothing. The sterile field will typically extend from operating table 24 upward in the operating room. Typically, both the computer display and fluoroscope display are located outside of the sterile field.

A representation of the patient's anatomy can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with the surgical navigation system 20 or by applying a statistical anatomical model. A morphed image of the patient's anatomy can be created by combining an image of the patient's anatomy with a data set, such as a virtual image of the patient's anatomy. Some imaging systems, such as C-arm fluoroscope 26, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-arm based navigation system is provided in James B. Stiehl et al., Navigation and Robotics in Total Joint and Spine Surgery, Chapter 3: C-Arm-Based Navigation, Springer-Verlag (2004).

Figure 2:
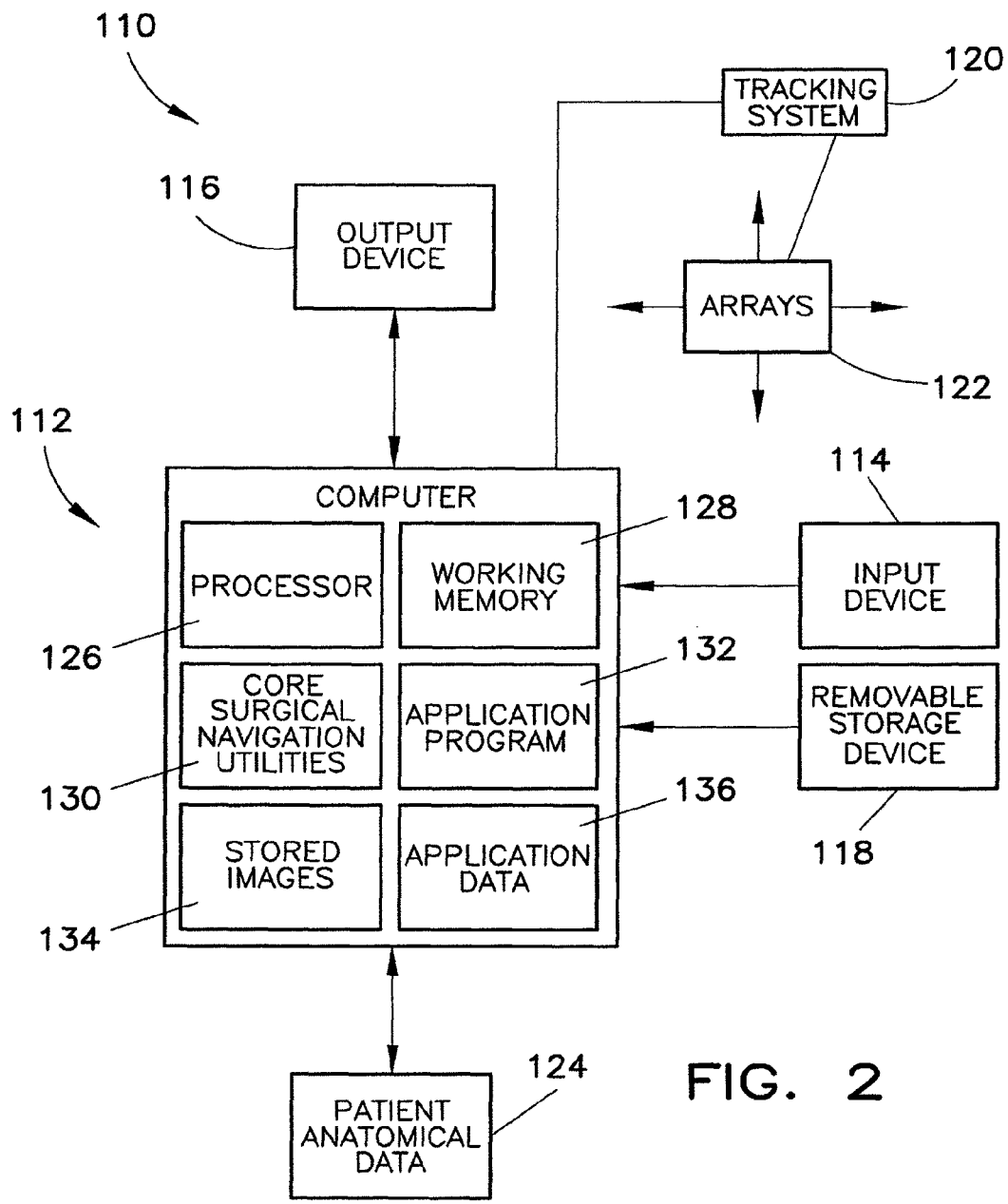
FIG. 2 is an exemplary block diagram of a surgical navigation system embodiment in accordance with the present teachings.

FIG. 2 is a block diagram of an exemplary surgical navigation system embodiment in accordance with the present teachings, such as an Acumen™ Surgical Navigation System, available from EBI, L.P., Parsippany, N.J. USA, a Biomet Company. The surgical navigation system 110 comprises computer 112, input device 114, output device 116, removable storage device 118, tracking system 120, arrays 122, and patient anatomical data 124, as further described in the brochure Acumen™ Surgical Navigation System, Understanding Surgical Navigation (2003) available from EBI, L.P. The Acumen™ Surgical Navigation System can operate in a variety of imaging modes such as a fluoroscopy mode creating a two-dimensional x-ray image, a computer-tomography (CT) mode creating a three-dimensional image, and an imageless mode creating a virtual image or planes and axes by defining anatomical points of the patient's anatomy. In the imageless mode, a separate imaging device such as a C-arm is not required, thereby simplifying set-up. The Acumen™ Surgical Navigation System can run a variety of orthopedic applications, including applications for knee arthroplasty, hip arthroplasty, spine surgery, and trauma surgery, as further described in the brochure "Acumen™ Surgical Navigation System, Surgical Navigation Applications" (2003), available from EBI, L.P. A more detailed description of an exemplary surgical navigation system is provided in James B. Stiehl et al., Navigation and Robotics in Total Joint and Spine Surgery, Chapter 1: Basics of Computer-Assisted Orthopedic Surgery (CAOS), Springer-Verlag (2004).

Computer 112 can be any computer capable of properly operating surgical navigation devices and software, such as a computer similar to a commercially available personal computer that comprises a processor 126, working memory 128, core surgical navigation utilities 130, an application program 132, stored images 134, and application data 136. Processor 126 is a processor of sufficient power for computer 112 to perform desired functions, such as one or more microprocessors. Working memory 128 is memory sufficient for computer 112 to perform desired functions such as solid-state memory, random-access memory, and the like. Core surgical navigation utilities 130 are the basic operating programs, and include image registration, image acquisition, location algorithms, orientation algorithms, virtual keypad, diagnostics, and the like. Application program 132 can be any program configured for a specific surgical navigation purpose, such as orthopedic application programs for unicondylar knee ("uni-knee"), total knee, hip, spine, trauma, intramedullary ("IM") nail/rod, and external fixator. Stored images 134 are those recorded during image acquisition using any of the imaging systems previously discussed. Application data 136 is data that is generated or used by application program 132, such as implant geometries, instrument geometries, surgical defaults, patient landmarks, and the like. Application data 136 can be pre-loaded in the software or input by the user during a surgical navigation procedure.

Output device 116 can be any device capable of creating an output useful for surgery, such as a visual output and an auditory output. The visual output device can be any device capable of creating a visual output useful for surgery, such as a two-dimensional image, a three-dimensional image, a holographic image, and the like. The visual output device can be a monitor for producing two and three-dimensional images, a projector for producing two and three-dimensional images, and indicator lights. The auditory output can be any device capable of creating an auditory output used for surgery, such as a speaker that can be used to provide a voice or tone output.

Removable storage device 118 can be any device having a removable storage media that would allow downloading data, such as application data 136 and patient anatomical data 124. The removable storage device can be a read-write compact disc (CD) drive, a read-write digital video disc (DVD) drive, a flash solid-state memory port, a removable hard drive, a floppy disc drive, and the like.

Tracking system 120 can be any system that can determine the three-dimensional location of devices carrying or incorporating markers that serve as tracking indicia. An active tracking system has a collection of infrared light emitting diode (ILEDs) illuminators that surround the position sensor lenses to flood a measurement field of view with infrared light. A passive system incorporates retro-reflective markers that reflect infrared light back to the position sensor, and the system triangulates the real-time position (x, y, and z location) and orientation (rotation around x, y, and z axes) of an array 122 and reports the result to the computer system with an accuracy of about 0.35 mm Root Mean Squared (RMS). An example of a passive tracking system is a Polaris® Passive System and an example of a marker is the NDI Passive Spheres™, both available from Northern Digital Inc. Ontario, Canada. A hybrid tracking system can detect active and active wireless markers in addition to passive markers. Active marker based instruments enable automatic tool identification, program control of visible LEDs, and input via tool buttons. An example of a hybrid tracking system is the Polaris® Hybrid System, available from Northern Digital Inc. A marker can be a passive IR reflector, an active IR emitter, an electromagnetic marker, and an optical marker used with an optical camera.

As is generally known within the art, implants and instruments may also be tracked by electromagnetic tracking systems. These systems locate and track devices and produce a real-time, three-dimensional video display of the surgical procedure. This is accomplished by using electromagnetic field transmitters that generate a local magnetic field around the patient's anatomy. In turn, the localization system includes magnetic sensors that identify the position of tracked instruments as they move relative to the patient's anatomy. By not requiring a line of sight with the transmitter, electromagnetic systems are also adapted for in vivo use, and are also integrable, for instance, with ultrasound and CT imaging processes for performing interventional procedures by incorporating miniaturized tracking sensors into surgical instruments. By processing transmitted signals generated by the tracking sensors, the system is able to determine the position of the surgical instruments in space, as well as superimpose their relative positions onto pre-operatively captured CT images of the patient.

Arrays 122 can be probe arrays, instrument arrays, reference arrays, calibrator arrays, and the like. Arrays 122 can have any number of markers, but typically have three or more markers to define real-time position (x, y, and z location) and orientation (rotation around x, y, and z axes). An array comprises a body and markers. The body comprises an area for spatial separation of the markers. In some embodiments, there are at least two arms and some embodiments can have three arms, four arms, or more. The arms are typically arranged asymmetrically to facilitate specific array and marker identification by the tracking system. In other embodiments, such as a calibrator array, the body provides sufficient area for spatial separation of markers without the need for arms. Arrays can be disposable or non-disposable. Disposable arrays are typically manufactured from plastic and include installed markers. Non-disposable arrays are manufactured from a material that can be sterilized, such as aluminum, stainless steel, and the like. The markers are removable, so they can be removed before sterilization.

Planning and collecting patient anatomical data 124 is a process by which a clinician inputs into the surgical navigation system actual or approximate anatomical data. Anatomical data can be obtained through techniques such as anatomic painting, bone morphing, CT data input, and other inputs, such as ultrasound and fluoroscope and other imaging systems.

Figure 3:
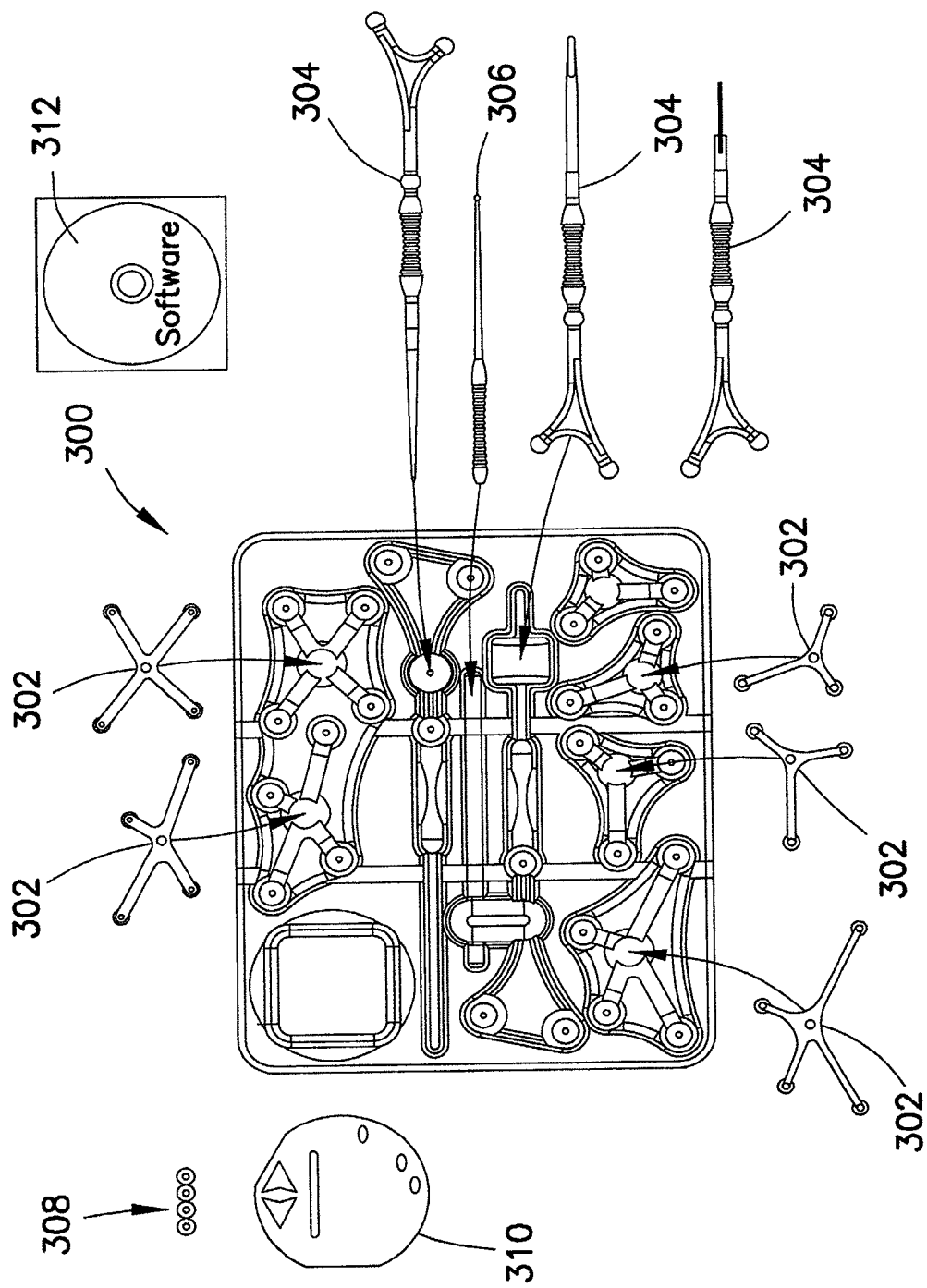
FIG. 3 is an exemplary surgical navigation kit embodiment in accordance with the present teachings.

FIG. 3 shows orthopedic application kit 300, which is used in accordance with the present teachings. Application kit 300 is typically carried in a sterile bubble pack and is configured for a specific surgery. Exemplary kit 300 comprises arrays 302, surgical probes 304, stylus 306, markers 308, virtual keypad template 310, and application program 312. Orthopedic application kits are available for unicondylar knee, total knee, total hip, spine, and external fixation from EBI, L.P.

The present teachings enhance surgical navigation system 20 by incorporating into the system a process for detecting bone abnormalities or defects with a diagnostic scope, and particularly to a process that can be used to custom manufacture a biomedical implant that is appropriately sized and shaped for implantation onto the flawed bone.

Figure 4:
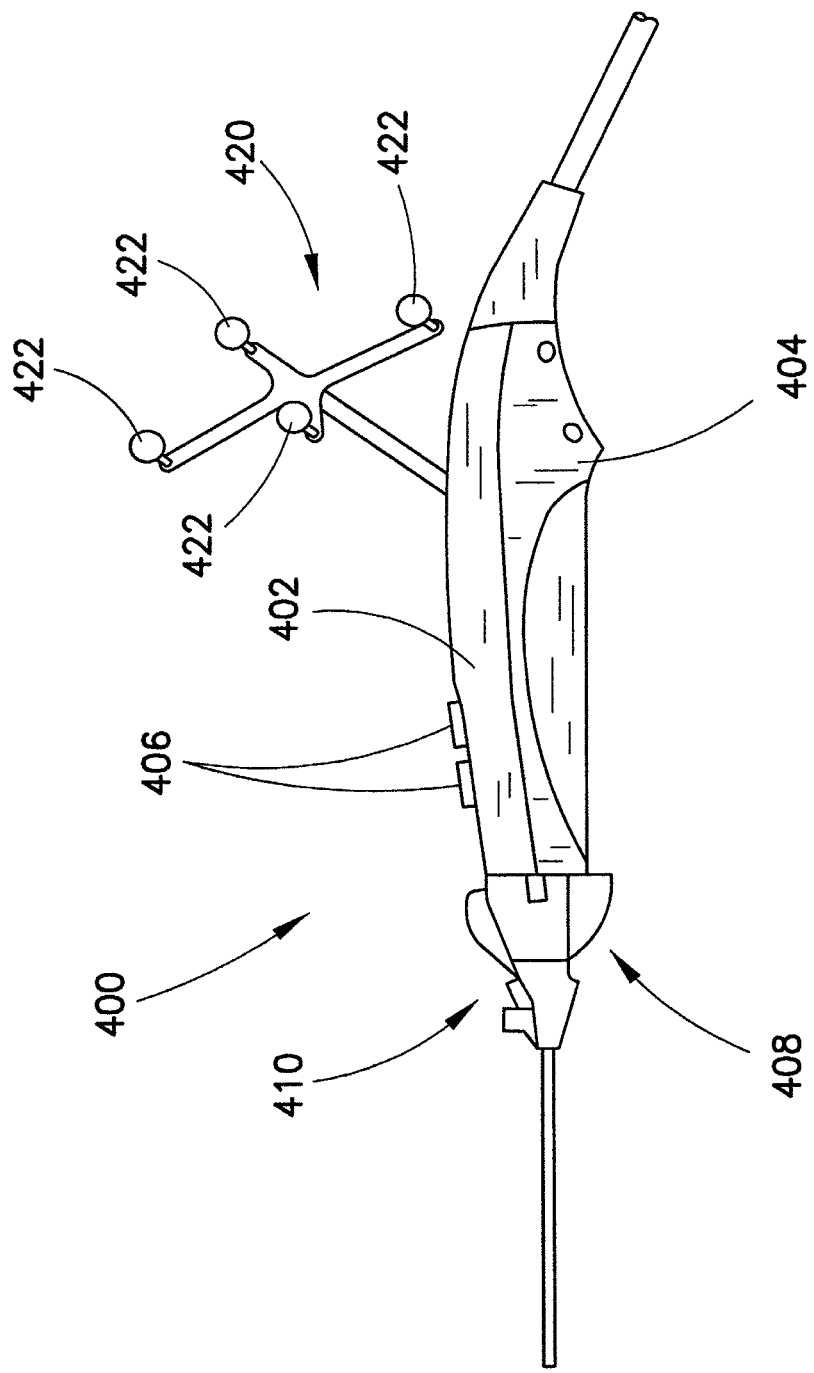
FIG. 4 is a perspective view of a diagnostic scope in accordance with the present teachings.

FIG. 4 illustrates an exemplary diagnostic scope assembly 400 for use with surgical navigation system 20. An example of such a diagnostic scope assembly that is useful with the present teachings is the InnerVue™ Camera Handpiece with Disposable Scope, which is used in conjunction with the InnerVue™ Diagnostic Scope System, available from Arthrotek®, Warsaw, Ind. USA, a Biomet Company. Here, diagnostic scope assembly 400 includes a housing 402 that forms a handpiece 404, which is ergonomically shaped so that a user can easily hold the assembly during a diagnostic scope procedure. The handpiece 404 further includes a camera and light source (not shown) housed within its structure, as well as one or more buttons 406, which can be programmed to allow the user to perform various navigational functions during the diagnostic procedure. For instance, in certain aspects of the present invention, buttons 406 may be used to capture or record images that are detected by the camera and light source, or they may be used to alternate between video and still images during the surgical procedures. One of skill in the art will understand and appreciate, however, that the buttons may be programmed to perform any number of surgical navigation functions without straying from the present teachings.

A fiber optic scope 408 (such as a 1.2 mm diagnostic scope) is also removably connected to the assembly 400 at one end. While the size of the fiber optic scope can vary depending on the surgical procedure to be performed, it should be understood that the scope should at least be sized so that it can easily penetrate the patient's body during the surgical diagnostic procedure. For instance, according to certain aspects of the present teachings, the removable fiber optic scope is approximately the size of an 18-gauge needle. Moreover, the fiber optic scope can also be disposable, as well as sterilely packaged in a single use pouch. To attach fiber optic scope 408 to assembly 400, any feasible attachment means may be used, such as, but not limited to, molding, fusing, threading, gluing, snapping, press-fitting or the like.

Fiber optic scope 408 is configured to house a cannula device 410 that mimics a needle or tube that can be inserted into a patient during a diagnostic procedure. As such, the size of the cannula device is typically the size of a gauge needle (e.g., about 1.9 mm in diameter). Cannula devices are generally known within the art and typically include a trocar, obturator and plug. Cannula device 410 is also formed of a molded plastic body having a stainless steel sheath to provide rigidity as the device is inserted into and maneuvered within the patient's body. Moreover, the cannula device may also have a luer port on its body to allow irrigation, and the plug may be configured to seal the scope port on the cannula during intra-articular injection.

Unlike traditional scope assemblies, scope assembly 400 further includes a reference array 420 that enables the surgical navigation system to locate and track in real-time the position of the scope assembly relative to other arrays and/or surgical instruments within the surgical field. More particularly, the tracking system determines the position of scope assembly 400 by detecting the position of markers 422 on reference array 420 in space using known triangulation methods. The relative location of scope assembly 400 can then be shown on a surgical plan image of a computer display positioned within the surgical field.

Figure 5:
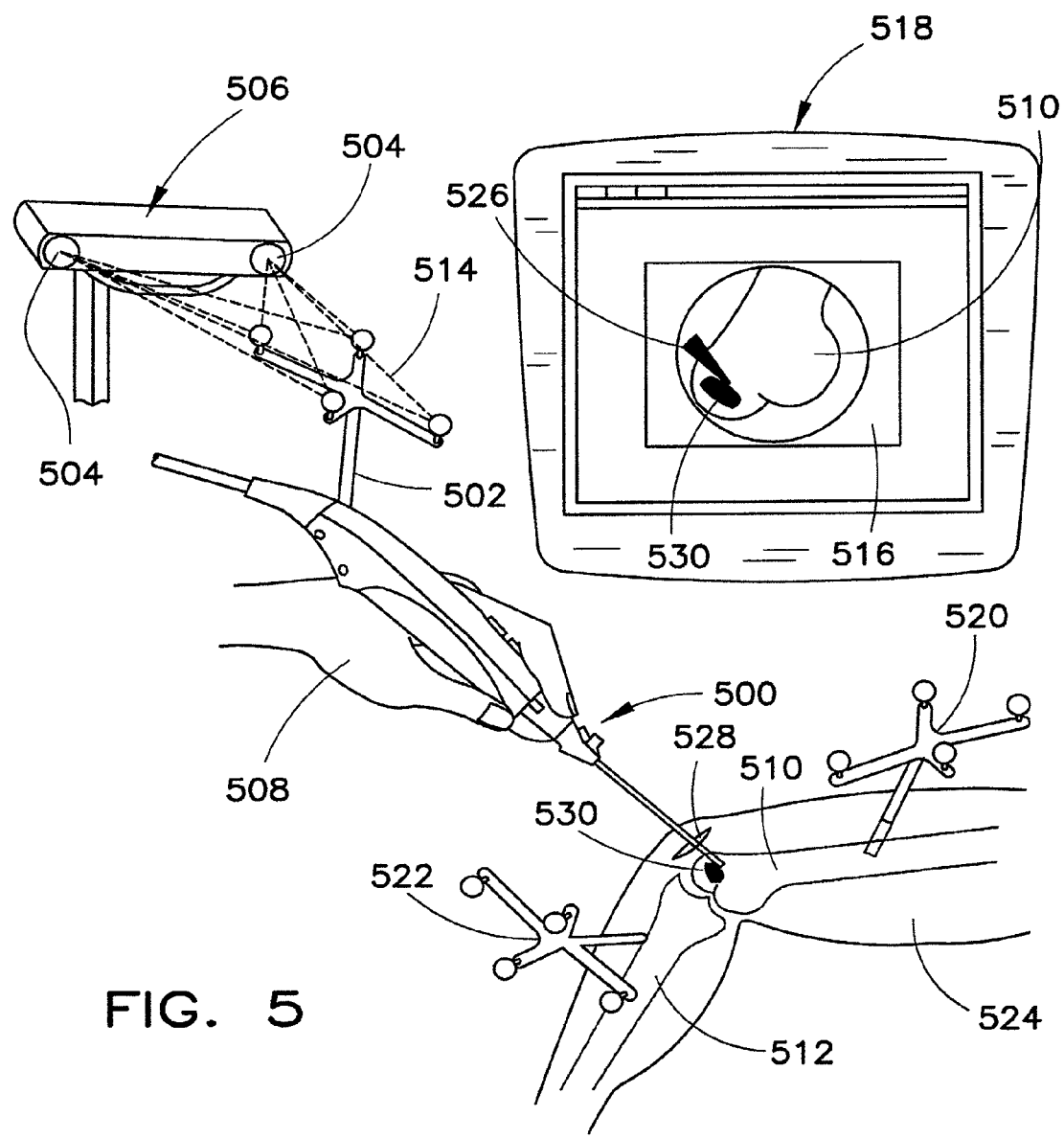
FIG. 5 is a fragmentary perspective view of a surgeon identifying a bone abnormality in accordance with the present teachings.

The principles upon which exemplary embodiments of the present invention rely can be understood with reference to FIG. 5, which illustrates a diagnostic scope assembly 500 identifying a bone defect or abnormality on a bone. Assembly 500 includes reference array 502, which is identified and tracked by cameras 504 of optical locator 506. As surgeon 508 moves scope assembly 500 relative to bones 510 and 512, the tracking system locates and tracks reference array 502 in real-time (see the optical path/measurement field of the tracking system represented by dashed lines 514). To accomplish this, cameras 504 of optical locator 506 detect the position of reference array 502 in space by using triangulation methods as discussed above.

The tracking system detects the location of scope assembly 500 relative to bones 510, 512 by referencing the position of reference array 502 as it moves with respect to reference arrays 520 and 522, which are fixably attached to the femur and tibia of patient 524. As shown in FIG. 5, the position of scope assembly 500 is displayed on surgical plan image 516 as icon 526. It should be understood that the surgical plan image shown on computer display 518 is merely intended to illustrate general principles, and is not representative of any particular "screen shot" that a surgeon may view during a surgical navigation procedure. For instance, the images that would typically be observed on a surgical plan image during a knee diagnostic scope procedure would likely be unintelligible to a layperson, particularly as the light source of the scope creates bright and shadowed areas of cartilage, bone, endothelium, blood and other fluids and structures, which are typically only recognizable to trained surgeons. Thus, to illustrate the principles of the present teachings, the surgical plan images depicted within the figures have been simplified so that the general teachings of the present procedures can be clearly represented and understood.

Once scope assembly 500 has been inserted into the patient's knee at the incision site (see the opening in the patient's knee indicated by reference numeral 528), the patient's bones 510, 512, as well as the interior of the knee joint and all its compartments become visible to the surgeon on surgical plan image 516. At this point, the surgeon is now able to freely move the scope around inside the incision cavity and thereby view real-time images of the patient's bones and ligaments. Such efforts allow the surgeon to identify any unnatural surface defects, flaws or abnormalities that may be present within the patient's knee region. For instance, in FIG. 5, surgical plan image 516 is depicting surface defect 530, which surgeon 508 has located on bone 510 (i.e., the patient's femur bone). While FIG. 5 generally depicts the surface defect as a darkened cavity, it should be understood and appreciated herein that any type of surface defect or abnormality may be identified in accordance with the present teachings. For instance, exemplary surface defects may include, but are not limited to, anatomical variants, lesions, cracks, cavities, divots, grooves, pits, holes, bumps, ridges or any other type of anatomical abnormality that is atypical in terms of size, location, shape and/or morphology. It should also be understood that such surface defects are capable of being discovered during a pre-operative diagnostic procedure or x-ray or during the actual diagnostic scope procedure (i.e. intra-operatively) being described herein.

While not shown here, additional monitors may also be used to display other images of the patient's anatomy during the diagnostic scope procedure. For instance, it may be desirable to display other endoscopic images of the patient's anatomy that were taken during the instant procedure and/or images that were taken during a previous procedure. It should be understood that these images can be captured by any known imaging methodologies available within the surgical navigation art. Such imaging methodologies include, but are not limited to, fluoroscopy, computer tomography (CT), magnetic resonance imaging (MRI), ultrasound, and the like.

After surface defect 530 has been located, surgeon 508 can utilize scope assembly 500 to register or collect a series of points on the bone to define the general shape, location and dimensional parameters of the defect. To register or collect these points, a navigational application program is typically used which arranges the point acquisition process into sequential pages of surgical protocol that are configured according to a graphic user interface scheme. For instance, in FIG. 6 surgeon 508 has touched scope assembly 500 against the surface of femur 510 at a plurality of locations 540 (shown as a series of black dots surrounding defect 530) surrounding the periphery of surface defect 530. As the surgeon positions the scope assembly at these various points, the tracking system tracks markers 542 on reference array 502 with cameras 504 of optical locator 506 and detects the position of the markers in space. As the tracking system detects the position of the markers in space, it analyzes the relative spatial position coordinates that correspond to the plurality of select locations 540 along the surface of femur 510 by using algorithms to reconstruct 3D coordinates of each of the detected reference array markers 542. Because the surgeon registers a series of points corresponding to the circumference or periphery of the defect, an approximate reading of the defect's dimensional parameters (i.e., its general size, shape, etc.) can be gathered by the system and collected for further analysis as needed.

To detect the location of scope assembly 500 relative to femur 510 and tibia 512, the tracking system references the position of markers 542 as they move with respect to reference arrays 520 and 522, which are fixably attached to the femur and tibia of the patient. By tracking the relative position of the markers, the exact location of the individual points corresponding to the acquired locations 540 can be determined and shown on the surgical plan image (shown here as black dots 544 on surgical plan image 516). Once the assembly is positioned at a specific point to be acquired, the point can be selected or registered with the system by blocking the markers 542 of the scope assembly from the camera (e.g., selective gesturing) or by any other input means, such as by pushing or selectively activating one of the buttons 546 on the scope assembly or one or more buttons on a conventional computer mouse or keyboard (not shown) that is associated with the navigation system. By pushing a button on the scope assembly, a mouse or a keyboard, the navigation system can be programmed to instantaneously capture the exact location of markers 542 in real-time and translate this position into the surgical plan image.

Selective gesturing is a procedure that allows a user to make a virtual mouse input by occluding the optical path (e.g., the optical path shown in FIG. 6 by dashed lines 514) between tracked optical markers and the cameras of an optical locator. For instance, by occluding the optical path for a certain period-of-time, the tracking system can recognize the action as being equivalent to a click of a left mouse button on a conventional computer mouse. It is also within the scope of the present teachings to perform a double click on a button by occluding the optical path for a period of time, unblocking the optical path for a period of time, blocking the optical path again for a period of time and then unblocking the optical path. For a further description of selective gesturing, see U.S. patent application Ser. No. 11/290,267, entitled "Selective Gesturing Input to a Surgical Navigation System," filed Nov. 30, 2005, which is incorporated by reference herein in its entirety.

The system may also recognize and assign functionality to movement of the tip of scope assembly 500 away from the surface of a bone, i.e., along the z-axis. For example, a quick movement of the tip of the scope assembly away from femur 510 a few centimeters and then returning the tip to substantially the same spot on the femur may be interpreted as being equivalent to a single click of a conventional mouse. Similarly, two of these short "taps" may be interpreted as a double click. One of skill in the art would readily recognize many other functions or mouse inputs that could be assigned to various movements of the scope in the z-axis without straying from the present teachings. For a further description of virtual mouse inputting operations useful in accordance with the present teachings, see U.S. patent application Ser. No. 11/227,741, filed Sep. 15, 2005, entitled "Virtual Mouse for use in Surgical Navigation" and U.S. patent application Ser. No. 11/434,035, filed May 15, 2006, also entitled "Virtual Mouse for use in Surgical Navigation," both disclosures of which are incorporated by reference herein in their entirety.

According to one aspect of the present teachings, after capturing the plurality of locations 540 on or near surface defect 530, software associated with the tracking system can collect and analyze the data and define the dimensional parameters of the abnormality (i.e., its size, shape, location, etc.). More particularly, the acquired points can be analyzed by the software program, which can then determine what implant component would be appropriate for correcting the defect. As will be described in detail below, a custom manufactured implant component can alternatively be created if the software program is not configured to suggest an implant component and/or the software program is unable to locate an implant component that is appropriately shaped and sized to correct the surface defect as needed.

Figure 6:
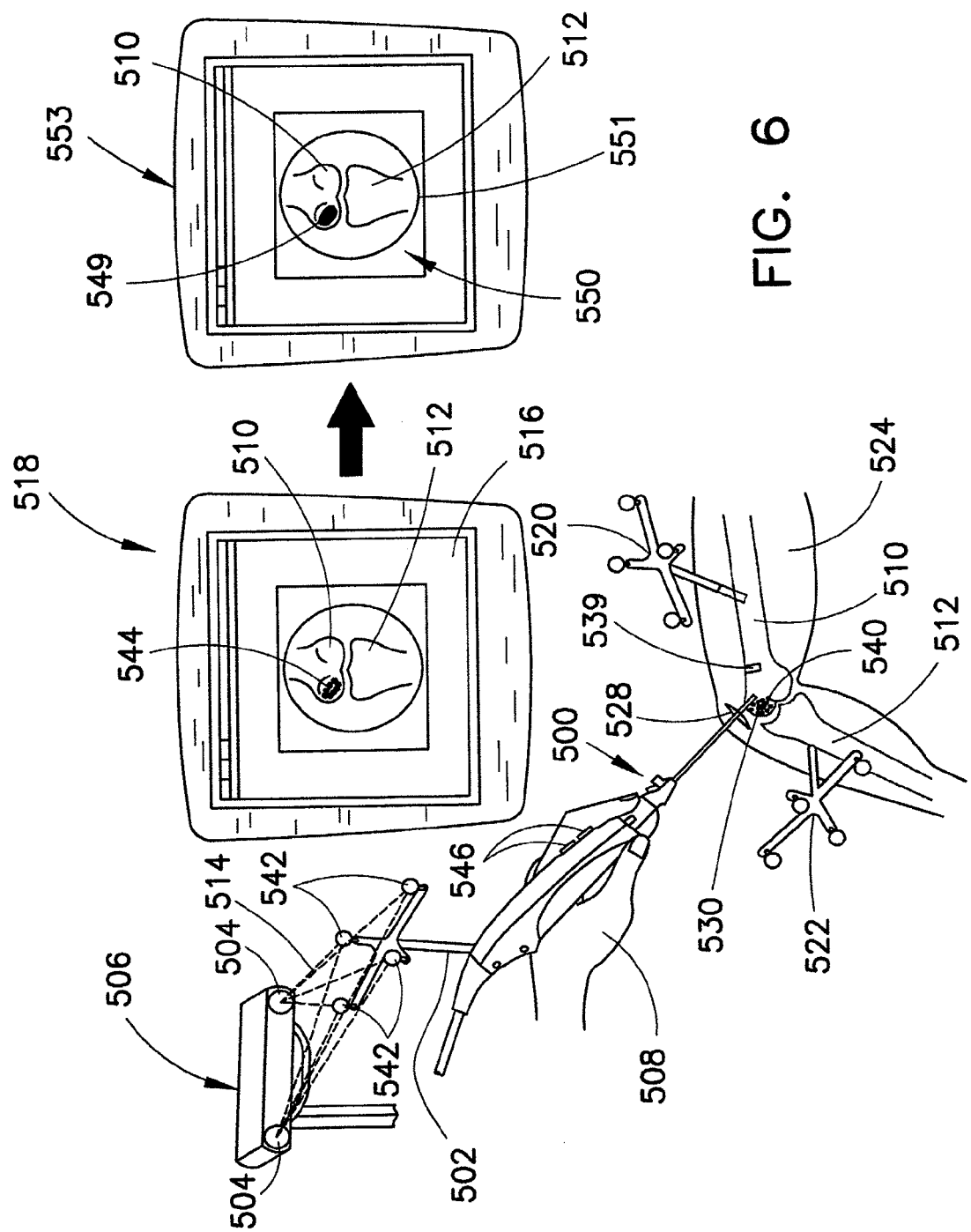
FIG. 6 is a fragmentary perspective view of a surgeon identifying and registering a series of points surrounding the bone abnormality of FIG. 5.

According to another aspect of the present teachings, after capturing the plurality of locations 540 on or near the surface defect, a three-dimensional model of the surface defect can optionally be generated on the surgical plan image. For instance, as shown in FIG. 6, the captured points taken at the plurality of locations 540 along femur 510 are shown in three-dimensional model 550 on surgical plan image 551 of computer monitor 553. By showing three-dimensional model 550, and particularly a representation of the bone defect on the three-dimensional model (i.e., see the blackened area 549 on the three-dimensional model), surgeon 508 is able to quantitatively evaluate and analyze the dimensional parameters and morphology of the defect. Moreover, the surgeon can use the model as a visual aid and manipulate it intra-operatively to perform the diagnostic procedure or to gather important surgical information, such as gap analysis data, resection plane details and bone alignment angles. Additionally, plan image 551 can be split into various sections showing the three-dimensional model from various perspectives. As such, if the surgeon desires, he can rotate and/or manipulate the model so that its general shape and characteristics can be visually appreciated. Moreover, by collecting fewer or more points, the surgeon can tailor the precision of three-dimensional model 550 based on the clinical relevance of any given abnormality.

If desired, a fiducial marker may be placed into the bone at or near the defect so that measurements taken in one procedure can be accurately overlaid on images acquired in a later procedure. The fiducial marker could be any stationary device that would provide a reproducible point of reference in aligning the navigation system. For example, the fiducial maker might be a screw, pin or device (e.g., see the fiducial device inserted into femur 510, which is indicated by reference numeral 539) inserted into the bone at some distance from the surgical site so as not to be disturbed during the surgical procedure. The surgeon can also mark the area surrounding the defect for later reference in a subsequent procedure if desired. As such, it should be understood and appreciated herein that there are a variety of acceptable ways to define the three-dimensional reference space surrounding the defect for further reference and identification.

Figure 7:
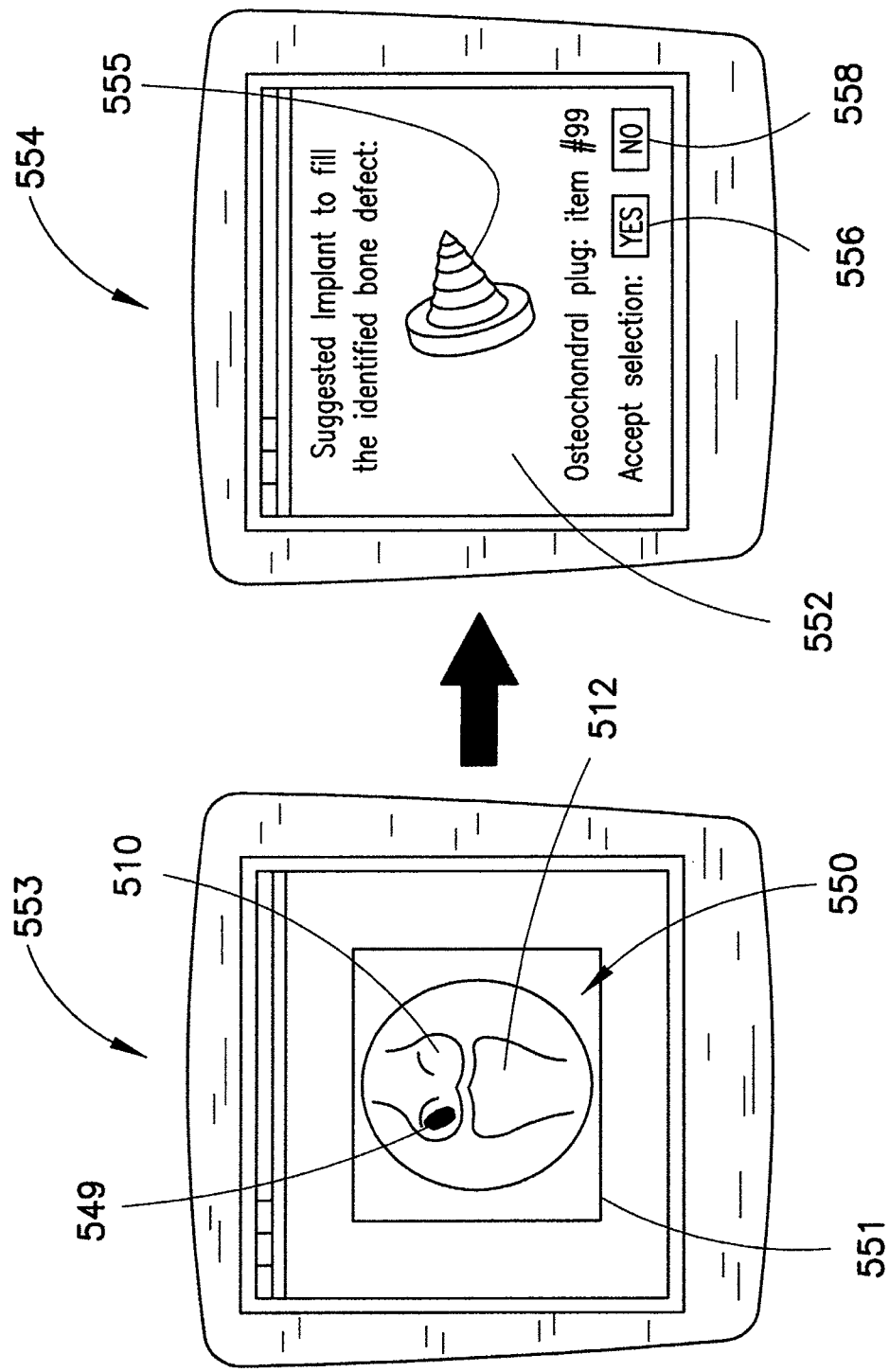
FIG. 7 shows exemplary computer navigation screens in accordance with the present teachings.

Once the system has calculated the dimensional parameters of the surface defect 530, the data is then analyzed by a software program, which is configured to determine what biomedical implant can be implanted into or onto the flawed bone to correct or fill the bone defect. For instance, as shown on surgical plan image 552 of computer monitor 554 (see FIG. 7), the software program can generate a virtual image of one or more generic implant models stored within a computer database that can be used for the implantation process. For instance, in FIG. 7, the database has identified osteochondral bone plug 555 as being an appropriate implant prosthetic to be implanted onto femur 510 to fill defect 530. More particularly, after mapping the dimensional parameters of surface defect 530 and creating three-dimensional model 550, the computer system's database has determined that bone plug 555 most closely resembles the physical dimensions of the bone flaw, and therefore would be an appropriate component for implanting into the bone to correct the defect. According to this embodiment, surgeon 508 is then prompted to select whether this closest matching implant is acceptable or not for the procedure to be performed. If the suggested implant match is correct, the surgeon can select "yes" button 556 on monitor 554, whereby the software program will then provide any known surgical information that is appropriate for a surgical procedure involving bone plug 555. Alternatively, if the suggested implant match generated by the software program is inappropriate, the surgeon can select "no" button 558, whereby the system can then prompt the surgeon to select another close match or alternatively allow the surgeon to manually enter or record the dimensional surface data into the database to be stored as a new entry. This stored information can then be used to manufacture a customized implant that would more closely fit the general shape and contour of the patient experiencing the surface flaw.

To expand upon the above process, in a diagnostic procedure, the surgeon can transmit the data defining the defect or abnormality to an implant manufacturer that can produce a custom-fit prosthesis. More particularly, once the points on and surrounding the surface defect are identified and recorded by the computer system, an implant can be custom manufactured to match the patient's defect. According to this embodiment, the surgeon, in a follow-up procedure, will utilize information gathered during previous diagnostic procedures to register the patient's anatomy as needed. This is accomplished by utilizing as a reference system the surface of the bone and the points previously utilized during the prior procedure. The defect area is prepared and the patient matched implant can then be placed either with or without tracking the component.

Figure 8:
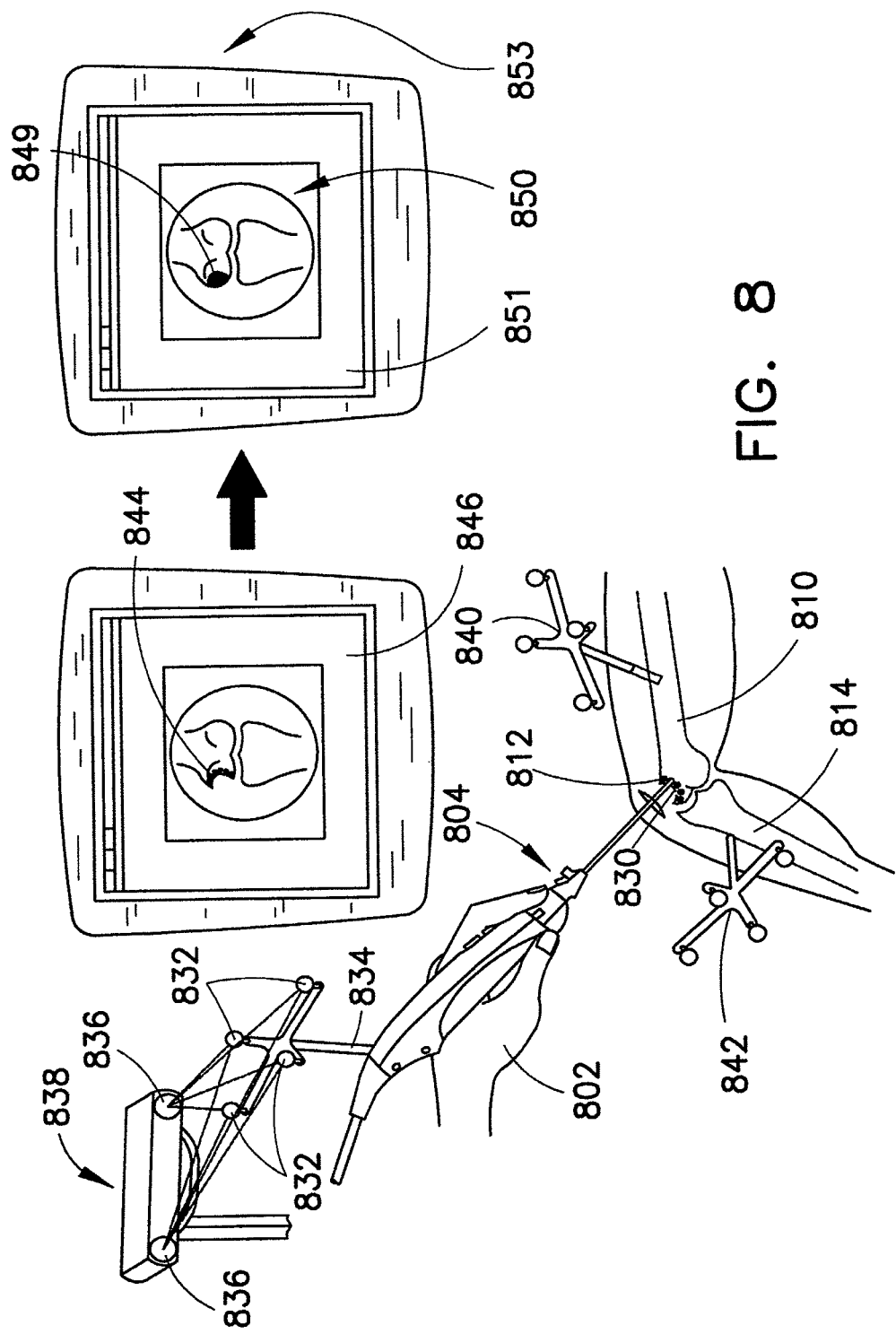
FIG. 8 is a fragmentary perspective view showing a surgeon identifying and registering a series of points surrounding a bone abnormality in accordance with an exemplary process of the present teachings.

FIG. 8 depicts an exemplary process for custom manufacturing an implant in accordance with the present teachings. More particularly, surgeon 802 uses scope assembly 804 to touch the surface of femur 810 at a plurality of locations 812 (shown as a series of black dots surrounding defect 830) surrounding the periphery of surface defect 830. As the surgeon positions the scope assembly at these various points, the tracking system tracks and detects in space the position of markers 832 on reference array 834 with cameras 836 of optical locator 838. As the tracking system detects the position of the markers in space, it analyzes the relative spatial position coordinates that correspond to the plurality of select locations 812 along the surface of femur 810 by using algorithms to reconstruct 3D coordinates of each of the detected reference array markers 832.

As discussed in detail above, the tracking system detects the location of scope assembly 804 relative to femur 810 and tibia 814 by referencing the position of markers 832 as they move with respect to reference arrays 840 and 842, which are fixably attached to the femur and tibia of the patient. By tracking the position of the markers relative to femur 810, the exact location of the acquired locations 812 can be determined and shown on the surgical plan image (shown here as black dots 844 on surgical plan image 846). As mentioned above, the specific points can be acquired by many different capturing means, such as, but not limited to selective gesturing techniques, pressing a button on the scope assembly, a mouse or a keyboard and/or tapping the tip of the scope assembly relative to the bone's surface.

After capturing the plurality of locations 812 on or near surface defect 830, a three-dimensional model of the surface defect can be generated on the surgical plan image. For instance, as shown in FIG. 8, the captured points taken at the plurality of locations 812 along femur 810 are shown in three-dimensional model 850 on surgical plan image 851 of computer monitor 853. By showing three-dimensional model 850, and particularly a representation of the bone defect on the three-dimensional model (i.e., see the blackened area 849 on the three-dimensional model), surgeon 802 is able to quantitatively evaluate and analyze the dimensional parameters and morphology of the defect.

As discussed above, after the data defining the defect or abnormality has been identified by the surgeon, this data can be transmitted to an implant manufacturer who can produce a custom-fit prosthesis. For instance, FIG. 9a depicts custom-fit knee prosthetic component 900 that has been designed to fit the femur of the patient from FIG. 8. More particularly, component 900 has a general shape and curvature that is precisely the same as the dimensional parameters exhibited by defect 830 of femur 810. Upon aligning component 900 with defect 830 (see FIG. 9b), the surgeon can be assured that the prosthetic component will comfortably align with the surface of femur 810 in a flush manner. FIG. 9c depicts prosthetic component 900 after it has been implanted onto femur 810. Because of the custom-fit nature of the prosthetic component, the longevity of the implant's useful life may be extended, particularly because the custom-fit component is not as susceptible to the normal wear and tear experienced by improperly sized and fitted implants.

While exemplary embodiments incorporating the principles of the present teachings have been disclosed hereinabove, the present teachings are not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of performing a surgical procedure, comprising:
    providing a tracking system and a diagnostic scope having a reference array attached thereto, the reference array having a reflective marker that is trackable by the tracking system;
    inserting a portion of the diagnostic scope into a body cavity through an incision site;
    identifying an abnormality on a bone within the body cavity with the diagnostic scope, wherein the diagnostic scope includes a grippable handle having a button actuatable by a hand gripping the handle;
    acquiring and registering a plurality of points on or near the abnormality with the diagnostic scope by detecting a position of the reflective marker attached to the diagnostic scope in space during each point acquisition, wherein the position of the reflective marker is detected in response to actuating the button on the grippable handle;
    capturing a real-time image of the bone with the diagnostic scope as the button on the grippable handle is actuated; and
    using the acquired plurality of points to make an implant having a portion whose shape substantially matches that of the bone abnormality.

2. The method of claim 1, wherein the acquisition of the plurality of points on or near the abnormality with the diagnostic scope comprises collecting and analyzing dimensional data of the abnormality.

3. The method of claim 2, wherein the making of the implant having a portion whose shape substantially matches that of the bone abnormality comprises custom manufacturing the implant based on the collected and analyzed dimensional data of the abnormality.

4. The method of claim 1, wherein the making of the implant having a portion whose shape substantially matches that of the bone abnormality comprises accessing a computer database containing one or more reference implant models.

5. The method of claim 1, further comprising generating a representative model of the bone abnormality from the acquired points.

6. The method of claim 5, wherein the representative model of the bone abnormality comprises a three-dimensional and manipulatable image of the bone abnormality, the image showing the acquired points.

7. The method of claim 1, further comprising inserting a fiducial marker into the bone at or near the abnormality so that images taken in a first procedure can be registered with images taken in a later procedure.

8. The method of claim 1, further comprising installing the implant onto the bone.

9. The method of claim 8, wherein the implant is installed onto the bone by using the tracking system.

10. The method of claim 1, wherein the bone abnormality is on a femur.

11. The method of claim 1, wherein the bone abnormality is on a tibia.

* * * * *